United States Patent [19]

Belanger et al.

[11] 4,341,904
[45] Jul. 27, 1982

[54] DERIVATIVES OF 2-HYDROXY-6,9-METHANO-11-AMINO-5,6,7,8,9,10-HEXAHYDRO-BENZOCYCLOOCTENE

[75] Inventors: Patrice C. Belanger, Dollard des Ormeaux; Robert N. Young, Senneville, both of Canada

[73] Assignee: Merck & Co., Inc., Rahway, N.J.

[21] Appl. No.: 117,701

[22] Filed: Feb. 19, 1980

[51] Int. Cl.$^3$ ............................................. C07C 87/40
[52] U.S. Cl. .................................. 564/427; 546/191; 546/204; 546/207; 546/208; 546/213; 546/214; 546/285; 548/301; 549/28; 549/60; 549/68; 564/167; 549/424; 549/426; 549/480; 549/492; 260/326.25; 260/326.33; 260/326.5 C; 260/326.5 M
[58] Field of Search ............... 260/571, 570.5 P, 570.6; 564/427, 374, 391

[56] References Cited

U.S. PATENT DOCUMENTS

| | | | |
|---|---|---|---|
| 3,499,906 | 3/1970 | Robinson et al. | 546/97 |
| 3,513,169 | 5/1970 | Robinson et al. | 546/97 |
| 3,514,463 | 5/1970 | Robinson et al. | 546/97 |
| 3,700,734 | 10/1972 | Robinson et al. | 546/97 |
| 3,836,670 | 9/1974 | Freed et al. | 260/571 X |
| 3,917,680 | 11/1975 | Potoski et al. | 260/571 |
| 4,001,331 | 1/1977 | Freed et al. | 260/571 |
| 4,008,277 | 2/1977 | Hewett et al. | 260/571 |
| 4,076,953 | 2/1978 | Freed et al. | 260/571 X |
| 4,156,694 | 5/1979 | Hewett et al. | 260/571 |

OTHER PUBLICATIONS

March, J., *Advanced Organic Chemistry*, McGraw Hill, New York, 1968, pp. 668–669, 675 and 899.
Chemical Abstracts, subject index vol. 88, p. 3008cs (1978).
Chemical Abstracts, 86:29529r (1977) [USP 3,957,872, Freed et al., 5/1976].
Froborg, J., et al., J. Org. Chem., 39 (6), 848–849 (1974).
Still, W., Synthesis, 453–454 (1976).
Opitz, G., et al., Ann. Chem., 650, 115–121 (1961).
Freed, M., et al., J. Med. Chem., 16(6), 595–599 (1973).

*Primary Examiner*—Richard A. Schwartz
*Attorney, Agent, or Firm*—Theresa Y. Cheng; Raymond M. Speer; Mario A. Monaco

[57] ABSTRACT

Novel amino derivatives of 2-hydroxy-6,9-methano-11-amino-5,6,7,8,9,10-hexahydro-benzocyclooctenes, methods for their preparation, and their use as effective analgesic agents is described.

2 Claims, No Drawings

DERIVATIVES OF 2-HYDROXY-6,9-METHANO-11-AMINO-5,6,7,8,9,10-HEXAHYDRO-BENZOCYCLOOCTENE

SUMMARY OF THE INVENTION

This invention relates to new amino derivatives of 2-hydroxy-6,9-methano-11-amino-5,6,7,8,9,10-hexahydrobenzocyclooctenes, processes for preparing the same, and methods of treatment using them as medicinal agents. The disclosed class of compounds in this invention has pronounced analgesic activity that is effective in the relief of pain.

BACKGROUND OF THE INVENTION

The most widely used drug to combat pain is still morphine. There are severe effects of this drug, however, for prolonged use of morphine generally leads to physiological and psychological dependency on the drug. In addition, it has a depressing effect on respiration. A tireless and expensive search for an analgesic that would be as potent as morphine, but free of its dangerous effects, has been carried on. Many analgesic disclosures related to the morphine model have been synthesized, the best known of which is pethidine. This was originally thought to be a non-addicting drug, but was soon found to have dangerous addiction liability. Other synthetic analgesics include a group of substances called benzomorphans. The best known member of this group is phenazocine, but like morphine, this is also dangerously addicting.

DESCRIPTION AND PREFERRED EMBODIMENTS

This invention relates to a new group of chemical compounds which are 11-amino and 11-carboxamido derivatives of 2,6,9-trisubstituted 6,9-methanobenzocyclooctenes and non-toxic pharmaceutically acceptable salts therof. This invention further relates to the novel methods of preparation of the instant trisubstituted 6,9-methano-benzobicyclooctenes.

The compounds of this invention can be represented by the following structural formula:

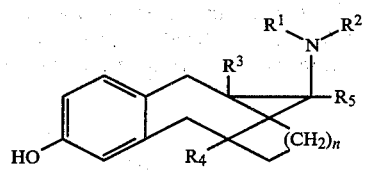

wherein $R^1$ and $R^2$ are each independently selected from the group consisting of hydrogen; alkyl (preferably lower alkyl such as methyl, ethyl, propyl, isopropyl, etc.); alkenyl (preferably loweralkenyl such as allyl, methallyl, 3-butenyl, etc.); cycloalkyl (preferably cycloloweralkyl such as cyclopropyl, cyclobutyl, etc.); cycloalkyl alkyl (preferably cycloloweralkyl lower alkyl such as cyclopropylmethyl, cyclopropylethyl, etc.); cycloalkenyl (preferably cycloloweralkenyl such as 2-cyclobutenyl, 3-cyclopentenyl, etc.); cycloalkenylalkyl (preferably cycloloweralkenyl lower alkyl such as 1-cyclobutenylmethyl, 2-cyclobutenylmethyl, etc.); alkylcycloalkyl (preferably loweralkylcycloloweralkyl such as methylcyclopropyl, ethylcyclopropyl, etc.); alkenylcycloalkyl (preferably loweralkenylcyclolower-alkyl such as methylenecyclopropyl, methylenecyclobutyl, 3-vinylcyclopentyl, etc.); alkylcycloalkenyl (preferably lower alkylcycloloweralkenyl such as 2,2,3-trimethylcyclopentyl, 2-methylcyclopentyl); phenyl; 5- and 6-membered heterocyclic wherein the heteroatom is nitrogen, oxygen, or sulfur; and said heterocyclic attached through $C_{1-2}$ alkyl;

$R_3$ and $R_4$ are each independently hydrogen or lower alkyl, preferably $C_{1-4}$ such as methyl, ethyl, propylisopropyl butyl, isobutyl;

$R_5$ is hydrogen, alkyloxymethyl, alkylamino, aralkylamino, N-substituted carboxamido, or aralkyloxymethyl in which the N substituent is benzyl, phenylethyl, or phenylpropyl; and n is 1 or 2.

Where n is 1, the benzocyclooctene structure is represented. Where n is 2, the structure is a 2-hydroxy-6,10-methano-5(H)-6,7,8,9,10,11-hexahydro-benzocyclononene. These structures, and their respective numberings, may be illustrated as follows:

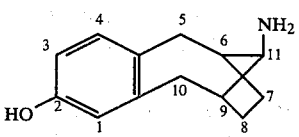

II

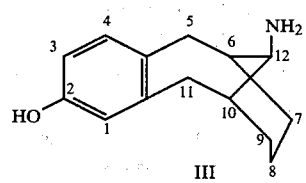

III

Included in this invention are the geometric isomers and diastereoisomers of the above-noted structure, which may vary to some extent in their biological activity.

These isomers can be separated into their optical isomers [dextra (+) and levo (−)] by preparing the diastereoisomeric salts with optically active acids either d(+) or l(−), which salts then can be separated by conventional methods such as fractional crystallization. Thus, it is to be understood that included in this invention, along with the novel 2,6,9-trisubstituted-2'-hydroxy-6,9-methanobenzocyclooctenes, are the individual optical isomers, that is the dextrorotatory (+) as well as the levorotatory (−) isomers of our novel benzocyclooctene compounds.

The more preferred aspects of this invention relate to benzocyclooctenes and the salts thereof, represented by the following formula:

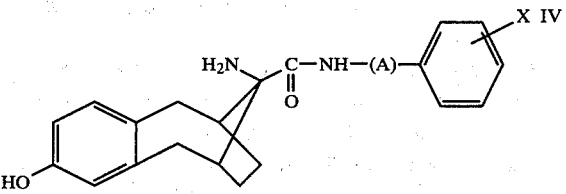

wherein A is absent or is a lower alkylene substituent of from 1-3 carbons, and X is hydrogen; halo; $C_{1-4}$alkyl; $C_{1-4}$alkoxy; amino, and mono- and di- $C_{1-4}$ alkyl substituted amino; cyano; trifluoromethyl; trifluoromethylthio; $C_{1-4}$ alkylthio; $C_{1-4}$ alkylsulfoxide; or $C_{1-4}$ alkylsulfone.

Another of the more preferred aspects of the present invention relates to benzocyclooctenes and the salts thereof represented by the following formula:

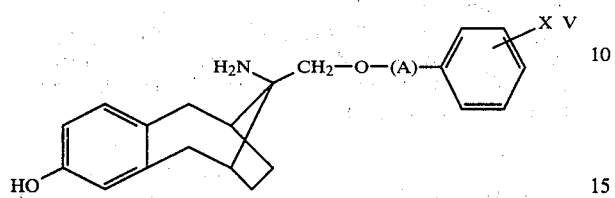

wherein A is absent or is a lower alkylene substituent of from 1-3 carbons, and X is hydrogen; halo; $C_{1-4}$alkyl; $C_{1-4}$alkoxy; amino, and mono- and di- $C_{1-4}$ alkyl substituted amino; cyano; trifluoromethyl; trifluoromethylthio; $C_{1-4}$ alkylthio; $C_{1-4}$ alkylsulfoxide; or $C_{1-4}$ alkylsulfone.

Representative compounds of this invention are 11-endo-amino-5,6,7,8,9,10-hexahydro-2-hydroxy-N-(2-phenylethyl)-6,9-methano-benzocyclooctene-11-carboxamide and derivatives thereof wherein the phenylethyl substituent is replaced by a p-halogen substituted phenylethyl substituent or the correspondingly substituted benzyl or phenyl propyl substituents.

Still other preferred aspects of this invention are benzocyclooctenes of the formula:

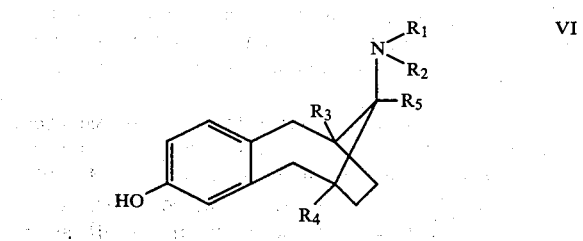

wherein $R_1$, $R_2$, $R_3$, and $R_4$ are as defined above, and $R_5$ is hydrogen, alkyloxymethyl, aralkyloxymethyl, alkylamino, or aralkylamino (preferably loweralkylamino of 1-4 carbons or diloweralkylamino of 2-8 carbons).

Representative compounds of this preferred aspect of the invention are:
- d,1-endo-11-amino-5,6,7,8,9,10-hexahydro-2-hydroxy-6,9-methano-benzocyclooctene hydrochloride;
- d,1-N,N-dimethyl-11-endo-amino-5,6,7,8,9,10-hexahydro-2-hydroxy-6,9-methanobenzocyclooctene;
- 11-endo-amino-5,6,7,8,9,10-hexahydro-6,9-methanobenzocyclooctene; and
- d,1-11-endo-amino-6,9-dimethyl-5,6,7,8,9,10-hexahydro-6,9-methanobenzocyclooctene.

A further aspect of this invention embraces a method of treatment for the relief of pain by the administration of compounds having the structural formula:

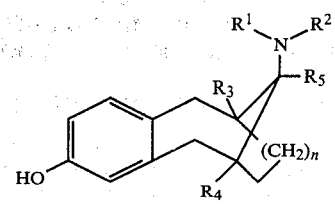

wherein $R^1$ and $R^2$ are each independently selected from the group consisting of hydrogen; alkyl (preferably lower alkyl such as methyl, ethyl, propyl, isopropyl, etc.); alkenyl (preferably loweralkenyl such as allyl, methallyl, 3-butenyl, etc.); cycloalkyl (preferably cycloloweralkyl such as cyclopropyl, cyclobutyl, etc.); cycloalkyl alkyl (preferably cycloloweralkyl lower alkyl such as cyclopropylmethyl, cyclopropylethyl, etc.); cycloalkenyl (preferably cycloloweralkenyl such as 2-cyclobutenyl, 3-cyclopentenyl, etc.); cycloalkenylalkyl (preferably cycloloweralkenyl lower alkyl such as 1-cyclobutenylmethyl, 2-cyclobutenylmethyl, etc.); alkylcycloalkyl (preferably loweralkylcycloloweralkyl such as methylcyclopropyl, ethylcyclopropyl, etc.); alkenylcycloalkyl (preferably loweralkenylcycloloweralkyl such as methylenecyclopropyl, methylenecyclobutyl, 3-vinylcyclopentyl, etc.); alkylcycloalkenyl (preferably lower alkylcycloloweralkenyl such as 2,2,3-trimethylcyclopentyl, 2-methylcyclopentyl); phenyl; 5- and 6-membered heterocyclic wherein the heteroatom is nitrogen, oxygen, or sulfur; and said heterocyclic attached through $C_{1-2}$ alkyl;

$R_3$ and $R_4$ are each independently hydrogen or lower alkyl, preferably $C_{1-4}$ such as methyl, ethyl, propylisopropyl butyl, isobutyl;

$R_5$ is hydrogen, alkyloxymethyl, alkylamino, aralkylamino, N-substituted carboxamido, or aralkyloxymethyl in which the N substituent is benzyl, phenylethyl, or phenylpropyl; and n is 1 or 2.

Included in this invention is the method of treatment for the relief of pain by the administration of compounds of the above structure and their optical isomers.

The most preferred aspects of this invention embrace a method of treatment for the relief of pain by the administration of compounds having the structural formula:

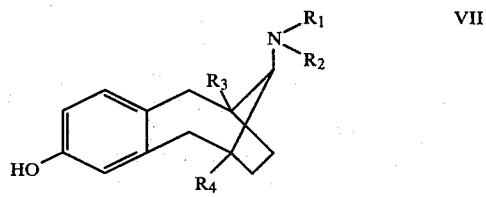

wherein $R^1$ and $R^2$ are each independently selected from the group consisting of hydrogen; alkyl (preferably lower alkyl such as methyl, ethyl, propyl, isopropyl, etc.); alkenyl (preferably loweralkenyl such as allyl, methallyl, 3-butenyl, etc.); cycloalkyl (preferably cycloloweralkyl such as cyclopropyl, cyclobutyl, etc.); cycloalkyl alkyl (preferably cycloloweralkyl lower alkyl such as cyclopropylmethyl, cyclopropylethyl, etc.); cycloalkenyl (preferably cycloloweralkenyl such as 2-cyclobutenyl, 3-cyclopentenyl, etc.); cycloalkenylalkyl (preferably cycloloweralkenyl lower alkyl such as 1-cyclobutenylmethyl, 2-cyclobutenylmethyl, etc.); alkylcycloalkyl (preferably loweralkylcyclolower alkyl such as methyl cyclopropyl, ethylcyclopropyl, etc.); alkenylcycloalkyl (preferably loweralkenylcyclolower alkyl such as methylenecyclopropyl, methylenecyclobutyl, 3-vinylcyclopentyl, etc.); alkylcycloalkenyl (preferably lower alkylcycloloweralkenyl such as 2,2,3-trimethylcyclopentyl, 2-methylcyclopentyl); and $R_3$ and $R_4$ are each independently hydrogen or lower alkyl, preferably $C_{1-4}$ such as methyl, ethyl, propylisopropyl butyl, and isobutyl.

The benzocyclooctene derivatives of this invention show good activity in a modified Randall Selitto test. Good activity in this test would indicate useful analgesic activity.

The benzocyclooctene derivatives of this invention generally have some narcotic antagonist activity as well as agonist activity. This mixture of agonist and antagonist activity can be advantageous since it is thought this will result in reduced side effects.

A further feature of this invention resides in the fact that the compounds of this invention can be produced by synthetic means more conveniently than are members of the morphine family of naturally occurring alkaloidal analgesics.

The compounds of this invention are administered orally or subcutaneously, preferably as an aqueous solution of the hydrochloride salt and in the range of about 1–100 mg./kg. per day.

Various tests in animals have been carried out to show the ability of the compounds of this invention to exhibit reactions that can be correlated with activity in humans. One such test as outlined by Charles A. Winter and Lars Flataker in The Journal of Pharmacology and Experimental Therapeutics, Volume 150, No. 1, pages 165–171, shows the ability of the instant compounds to exhibit analgesic effect. Measurements are made of the reaction threshold to pressure in the hind paws of rats injected with a phlogistic agent. These are compared with known analgesic drugs and marked increased effects can be found. Drug dosages of up to 18 mg./kg. are administered by the subcutaneous route. The experiments are carried out on Sprague-Dawley female rats weighing from 60 to 80 grams. The response threshold is determined by applying pressure to the foot and reading on a manometer the pressure at which an audible "squeak" is elicited. Groups of ten rats are used for each test and the average reading is recorded.

The benzocyclooctenes are conveniently prepared by the following method from known starting materials.

The starting materials are 5,6,7,8,9,10-hexahydro-6,9-methanobenzocyclooctene-11-one and are readily prepared by the reaction of $\alpha,\alpha'$-dihalo xylene or an appropriately substituted xylene and a cyclic ketone derivative. Thus, for example, reaction of $\alpha,\alpha'$-dibromo xylene and the pyrrolidine enamine of cyclopentanone or cyclohexanone in an aprotic such as acetonitrile produces the desired 6,9-methanobenzocyclooctene-11-one of the corresponding benzocyclononen-11-one. In order to introduce the phenolic hydroxyl group into the cyclooctene-11-one compounds in a one-step reaction, the starting ketone is treated in strongly acid solution, preferably in trifluoroacetic acid, with thallium trifluoroacetate at a temperature of from 0°–50° C. and preferably between 10°–30° C. The reaction is allowed to proceed for a period of from 1–24 hours and is then treated with an oxidizing agent, as for example lead tetraacetate, and the resulting mixture is then stirred with heating, preferably at reflux temperature of the reaction mixture for a period of from 1–5 hours. The entire reaction mixture is then treated with triphenyl phosphine in order to free the hydroxy cyclooctene-11-one from its complex, and then the desired ketone purified by removal of the reaction solvent by evaporation under reduced pressure followed by extraction of the residual material with chloroform, and the chloroform extract washed with water and dried to yield the desired product, which is conveniently purified by crystallization from a solvent.

The 11-keto compounds prepared according to the previous procedure are readily converted to the corresponding 11-amino compounds by conversion to the corresponding oximes, followed by catalytic reduction to the amine. Thus, for example, dl-5,6,7,8,9,10-hexahydro-2-hydroxy-6,9-methanobenzocyclooctene-11-one is converted to the corresponding 11-oximino compound by refluxing in the presence of an approximately equimolar amount of hydroxylamine hydrochloride. Following formation of the oxime, the reaction mixture is diluted with water and extracted to isolate the oxime, which is then further purified by chromatography on silica gel, followed by elution with chloroform containing traces of methanol.

Another process for the preparation of the corresponding N,N-dialkyl-11-endo-amino-6,9-methanobenzocyclooctene includes treatment of the corresponding cyclooctene-11-one directly with a mixture of an N,N-dialkyl amine and an alkali metal cyanoborohydride, preferably sodium cyanoborohydride, for a period of 1–4 days at a temperature of 0°–50° C. with direct production of the desired compound which may be purified by extraction with chloroform and recrystallization from a loweralkanol.

A process for the preparation of the compounds of the present invention which are substituted by alkyl substitutents, e.g., methyl substitutents in the 6 and/or 9 positions, begins with the treatment of an $\alpha,\alpha$-dihaloxylene with an alkylated or dialkylated derivative of the appropriate cycloalkanone-enamine. Thus, for example, $\alpha,\alpha$-dibromoxylene is treated with the pyrrolidine enamine of 2,5 -dimethylcyclopentanone to produce the corresponding 6,9-dimethyl-5,6,7,8,9,10-hexahydro-6,9-methanobenzocyclooctene-11-one, followed by thallation as described hereinabove, to introduce the corresponding 2'-hydroxy compound and subsequent conversion to the oxime, followed by catalytic reduction to the desired d,l-11- endo-amine-6,9-dimethyl-5,6,7,8,9,10-hexahydro-6,9-methanobenzocyclooctene.

In an alternate procedure for preparation of the N-substituted 11-carboxamidocyclooctene, the known starting ketone d,l-5,6,7,8,9,10-hexahydro-2'-hydroxy-6,9-methanobenzocyclooctene-11-one is treated in solution with sodium cyanide and ammonia to introduce an 11-amino and an 11-cyano substituent with resultant production of dl,-11-endo-amino-5,6,7,8,9,10-hexahydro-2'-hydroxy-6,9-methanobenzocyclooctene-11-exo-carbonitrile, which is hydrolyzed by treatment with a strong acid to produce the corresponding 11-exo-carboxylic acid. This 11-endo-amino-11-exo-carboxylic acid is then converted to the corresponding 11-endo formamido compound by treatment of the amino acid compound with a mixture of formic acetic anhydride in formic acid. The resulting d,l11-endo-formamido-5,6,7,8,9,10-hexahydro-2-hydroxy-6,9-methanobenzocyclooctene-11-carboxylic acid is converted to the corresponding mixed anhydride by treatment with ethyl chloroformate followed by reaction with 2-phenethylamine to produce the desired N-substituted amide d,l-11-endo-formamido-5,6,7,8,9,10-hexahydro-2′-hydroxy-N-(2-phenethyl)-6,9-methanobenzocyclooctene-11-carboxamide accompanied by a small amount of a cyclized reaction by-product (5′R,11′R) (5′S,11′S)-1′,2′,3′, 5′, 6′-hexahydro-8′-hydroxy-1-(2-phenylethyl)-spiro(1-H-imidazo-4,11′-(2,5)-methanobenzocyclooctene)-5(4H)-one.

The compounds of Formula V may be prepared by a procedure which employs as the starting material the d,l-11-endo-amino-11-exo-carboxy-5,6,7,8,9,10-hexahydro-2-hydroxy-6,9-methanobenzocyclooctene prepared as described in the paragraph immediately above. The starting material is first reduced with, e.g., diborane, to produce the corresponding 11-hydroxymethyl compound. The 11-endo-amino and 11-hydroxymethyl groups of this compound are then converted to an aziridine group by treating the compound with tosyl chloride. The tosylated compound of the second step is then added to the appropriate phenoxide or substituted phenoxide, or phenyl- or substituted-phenylalkoxide, which have, in turn, been prepared by reacting a 50% sodium hydride dispersion with the appropriate phenol or phenylalkanol. This step produces the desired compound, except for the tosyl group remaining on the 11-endo-amino substituent. This tosylamide is converted to the corresponding amine by treatment with sodium metal and liquid ammonia.

The following examples are provided for purposes of illustration and are not intended to be limitative of the invention.

EXAMPLE 1

Preparation of d,l-endo-11-Amino-5,6,7,8,9,10-hexahydro-2-hydroxy-6,9-methanobenzocyclooctene hydrochloride Step 1: 5,6,7,8,9,10-Hexahydro-6,9-methanobenzocycloocten-11-one The subject compound is prepared in accordance with the procedure described in the literature [Gunter Opitz and H. MildenBerger, Ann. 650, p, 115 (1961)], and has an m.p. of 89°–90° C. (literature m.p., 90°–91° C.).

Step 2: d,l-5,6,7,8,9,10-Hexahydro-2-hydroxy-6,9-methanobenzocycloocten-11-one

The ketone of Step 1 (1 g., 5.4 mM) is dissolved in trifluoroacetic acid (TFA) (10 ml.), and a solution of thallium tris-trifluoracetate (3.8 g., 7 mM) in TFA (20 ml.) is added, and the mixture is stirred overnight at ambient temperature. Lead tetraacetate (3.1 g., 7 mM) in TFA (10 ml.) is added, and the mixture is stirred one hour at room temperature and then refluxed for one hour. The mixture is cooled to room temperature, triphenylphosphine (1.9 g., 7.2 mM) is added, and after stirring 10 minutes, the solvent is removed in vacuo. 6 N HCl (50 ml.) is added, and after stirring 10 minutes, the mixture is filtered, and the filter cake is washed with chloroform (50 ml.). The organic layer is separated, and the aqueous layer is further washed with chloroform (3×20 ml.). The combined organic extracts are washed with 2 N NaOH (3×15 ml.). The basic extracts are combined, washed with chloroform (2×20 ml., discard), acidified (6 N HCl), and extracted with chloroform (5×15 ml.). The combined extracts are washed with brine (10 ml.), dried ($Na_2SO_4$), and reduced to dryness to yield a crystalline residue (600 mg.), which is recrystallized to yield 330 mg. of the subject compound, m.p. 188.5°–189° C. (ethyl acetate). Preparative tlcon the mother liquors ($CHCl_3$) gives an extra 210 mg. of pure compound. (Total yield, 50%.)

IR (KBr): 1720 $cm^{-1}$, 330 $cm^{-1}$ $^1$H-NMR ($CDCl_3$): 1.0-2,2 (4H, m); 2.4-3.0 (6H, m); 6.1 (1H, exchanged by $D_2O$, phenol OH), 6.5-7.2 ppm (3H, m).

mass spectrum: m/e 202 ($M^+$, peak base), 185, 174, 159, 148.

Anal. Calcd. for $C_{13}H_{14}O_2$: C, 77.20; H, 6.97. Found: C, 77.49; H, 7.13. $^{13}C$-NMR ($CDCl_3$) ppm: 22.7 (2C), 38.5, 39.5, 45.6, 45.8, 113.6, 119.1, 129.3, 133.3, 139.1, 154.6 (C=O not observed).

Step 3 Oxime of d,l-5,6,7,8,9,10-Hexahydro-2-hydroxy-6,9-methanobenzocycloocten-11-one The ketophenol of Step 2 (1.5 g., 7.4 mM) is refluxed in ethanol (15 ml.) and pyridine (4 ml.) with hydroxylamine hydrochloride (1.5 g. 22 mM) for 2 hours. The mixture is poured into water and extracted with chloroform. Theextracts are washed with water, dried ($Na_2SO_4$), and reduced to dryness in vacuo. The residue is chromatographed on silica gel (40 ml.). Chloroform containing a trace of methanol elutes the pure oxime (1.6 g.) (100%), m.p. 194° C.

IR (KBr): 1680 (C=N), 3400 $cm^{-1}$ (OH)

NMR ($CDCl_3$): 1.0-2.0 (4H, m); 2.9 (5H,broad s); 3.7 (1H, broad s); 5.4 (2H, broad, exchanged by $D_2O$), 6.5-7.2 ppm (3H, m).

mass spectrum: m/e 217 ($m^+$), 200, 185, 121.

EXAMPLE 2

Preparation of d,l-N,N-Dimethyl-11-endo-amino-5,6,7,8,9,10-hexahydro-2-hydroxy-6,9-methanobenzocyclooctene A mixture of d,l-5,6,7,8,9,10-hexahydro-2-hydroxy-6,9-methanobenzocyclooctene-11-one (1 g., 5 mM), dimethylamine (0.94 g., 20 mM), dimethylamine hydrochloride (800 mg., 10 mM), and sodium cyanoborohydride (270 mg., 6 mM) in dry methanol (13 ml.) is stirred 3 days at room temperature. The mixture is acidified with concentrated HCl, concentrated to remove methanol, and water is added (20 ml.). The mixture is heated with stirring, then cooled, and the resultant crystals are separated by filtration (1.1 g.). The filtrate is washed with ether (2×10 mg.), made basic with saturated $NaHCO_3$, and extracted with chloroform (3×15 ml.). The chloroform layers are washed with brine, dried, and evaporated to give a solid (220 mg.). This solid is dissolved in ethanol and made acidic with ethanolic HCl, then reduced to dryness and combined with the first crop of crystals. The combined material is recrystallized from ethanol to give analytically pure compound, m.p. 310°–312° C. (dec.).

IR (KBr): 3400, 3240, 2740, 2690, 2510, 2460 $cm^{-1}$.

$^1$H-NMR (MeOH-$d_4$): δ1.1-2.0 (4H, m), 2.4-3.7 (13H, m, 6H singlet at 3.0), 6.5-7.1 (3H, m).

Anal. Calcd. for $C_{15}H_{22}NOCl$: C, 67.28; H, 8.28; N, 5.23; Cl, 13.24. Found: C, 67.54; H, 8.48; N, 4.92; Cl, 13.68. The free base crystalizes from $CH_2Cl_2$-hexane as prisms, m.p. 143°–145° C.

EXAMPLE 3

Preparation of
d,l-11-endo-Amino-5,6,7,8,9,10-hexahydro-2-hydroxy-N-(2-phenylethyl)-6,9-methanobenzocyclooctene-11-carboxamide and (5'R, 11'R), (5'S, 11'S)-1',2',3',4',5',6'-hexahydro-8'-hydroxy-1-(2-phenylethyl)spiro(1H-imidazo-4,11'-(2,5)methanobenzocyclooctene)-5(4H)-one Step 1: d,l-11-endo-amino-5,6,7,8,9,10-hexahydro-2-hydroxy-6,9-methanobenzocyclooccten-11-exo-carbonitrile The ketophenol d,l-5,6,7,8,9,10-hexahydro-2-hydroxy-6,9-methanobenzocycloocten-11-one (2 g., 10 mM), ammonium chloride (1 g., 20 mM), sodium cyanide (1 g., 20 mM), concentrated ammonium hydroxide (20 ml.), and ammonia saturated methanol (20 ml.) are stirred together one-half hour and then left to stand overnight in the cold. The resultant crystals are collected (700 mg.) and are pure d,l-endo-11-amino-5,6,7,8,9,10-hexahydro-2-hydroxy-6,9-methanobenzocyclooctene-11-exo-carbonitrile. The filtrate is saturated with ammonia and left 2 days in the cold, yielding 350 mg. more subject compound. The filtrate is poured into water and extracted with ether (3×25 ml.). The ether extracts are washed with brine, dried ($Na_2SO_4$), and reduced to dryness to yield a solid (1.1 g.), essentially pure title compound by tlc. This solid plus 0.8 g. of the previously obtained crystals are used in the next reaction.

The reserved crystalline compound is recrystallized from chloroform-methanol to give an analytical sample m.p. 158°–160° C.

IR (KBr): 3380, 2220 $cm^{-1}$.

$^1$H-NMR (MeOH-$d_4$): 1.1-3.5 (10H, m), 6.3-6.9 (3H, m).

$^{13}$C-NMR (CD$_3$OD): 27.0 (2C), 34.2, 35.2, 45.9,(2C), 63.4, 113.7, 119.3, 127.2, 131.0, 133.4, 141.5, 156.5 ppm.

mass spectrum: m/e 228 (M+), 201, 200, 186, 173.

Anal. Calcd. for $C_{14}H_{16}N_2O$: C, 73.66; H, 7.06; N, 12.27. Found: C, 73.48; H, 7.27; N, 12.42.

Step 2: d,l-11-endo-Amino-5,6,7,8,9,10-hexahydro-2-hydroxy-6,9-methanobenzocycloocten-11-exo-carboxylic acid The aminonitrile of Step 1 above (1.9 g.) is dissolved in concentrated hydrochloric acid and saturated with HCl gas. The mixture is heated overnight in a pressure bottle at 95° C. The mixture is reduced to dryness in vacuo, taken up in water (25 ml.) and washed with ethylacetate (15 ml.) and chloroform (15 ml.), then filtered, and the water evaporated. The residue is dissolved in water and made slightly basic with ammonium hydroxide. The mixture is reduced to dryness, then slurried with water and reduced to dryness twice more before finally slurrying with water and filtering. The filter cake is washed with water several times, then quickly with cold acetone to dry, to yield the title amino acid (1.65 g.), m.p. 270°–275° C. (dec.).

IR (KBr): 1580-1630 (COO−), 2300-3600 $cm^{-1}$ ($NH_3^+$).

A portion (500 mg.) is treated with ethanolic HCl to dissolve, then reduced to dryness and recrystallized from methanol-chloroform to yield an analytical sample of the title compound hydrochloride (380 mg.), m.p. 297°–299° C. (dec.).

IR (KBr): 3600-2300, 1700 $cm^{-1}$.

H$^1$ NMR (MeOH-$d_4$): δ1.05 (2H, m), 1.85 (2H, m), 2.60 (6H, broad m), 6.30 (2H, m), 6.70 (1H, d, J=8 Hz).

$^{13}$C-NMR (MeOH-$d_4$): 27.6 (2C), 36.6, 37.5, 41.9, 42.1, 71.8, 114.4, 119.8, 129.0, 134.4, 139.5, 156.6, 173.6 ppm.

mass spectrum: m/e 248, 247 (M+), 202 (base peak, M+-COOH), 185, 121.

Anal. Calcd. for $C_{14}H_{17}NO_3$.HCl: C, 59.26; H, 6.37; N, 4.94; Cl, 12.49. Found: C, 59.41; H, 6.25; N, 5.24; Cl. 12.51.

Step 3: d,l-11-endo-Formamido-5,6,7,8,9,10-hexahydro-2-hydroxy-6,9-methanobenzocycloocten-11-carboxylic acid The aminoacid obtained in Step 2 above (1 g., 4 mM) in formic acid (2 ml.) is treated with a prepared solution of formic acetic anhydride (ca. 20 mole %) in formic acid (5 ml., ca. 20 mM anhydride), and the mixture is stirred 4 hours at room temperature. The solvents are removed under high vacuum to yield a brown solid (1.17 g.) essentially one spot on tlc analysis. A portion recrystallized from methanol-chloroform has m.p. 246°–248° C.

IR (KBr): 3600-2500 (COOH), 1720 (COOH), 1660 $Cn^{-1}$ (C=O,amide).

NMR (MeOH-$d_4$): δ1.0 (2H, m), 1.65 (2H, m), 2.0-3.0 (6H, m), 6.4 (2H, m), 6.75 (1H, d, J=8 Hz), 7.95 (1H, s, CHO).

mass spectrum: m/e 275 (M+), 257, 230, 202, 185, 184, 157.

Step 4 d,l-11-endo-Formamido-5,6,7,8,9,10-hexahydro-2-hydroxy-N-(2-phenylethyl)-6,9-methanobenzocyclooctene-11-carboxamide The N-formylamino acid of Step 3 (280 mg., 1 mM) is dissolved in dichloromethane (10 ml.) and triethylamine (1 ml.) and cooled to 0° C. Ethylchloroformate (260 μl., 2.4 mM) is added; and after stirring 1 hour at 0° C., 2-phenethylamine (220 μl., 2 mM) is added and stirring is continued overnight at ambiant temperature. The mixture is diluted with chloroform (25 ml.), then washed with 20% citric acid (10 ml.), saturated sodium bicarbonate (10 ml), then dried ($Na_2SO_4$), and reduced to dryness to yield a residue which is taken up in methanol and 1 N NaOH and stirred 1 hour at room temperature. The mixture is diluted with chloroform and poured into 20% citric acid (excess) and the organic layer is separated. The aqueous layer is extracted with chloroform (3 times), and the combined organic extracts are dried ($Na_2SO_4$) and reduced to dryness to yield a solid (380 mg.). The mixture is recrystallized from methanol-chloroform to yield pure title compound (230 mg.), m.p. 233°–235° C. Preparative tlc on the mother liquors yields a further 40 mg. of the title compound. (Total yield, 70%.)

IR (KBr): 3300, 1650 $cn^{-1}$.

NMR (CDCl$_3$-MeOH-$d_4$): δ0.8-1.7 (m), 2.3-3.7 (10H, m), 6.5 (2H, m), 6.8 (1H, d, J=8 Hz), 7.20 (6H, s, φ and amide NH), 7.4 (1H, m, amide NH), 8.05 (1H, s, —CHO).

mass spectrum: m/e 378 (M+), 360, 305, 230, 185 (base peak).

Step 5: d,l-11-endo-amino-5,6,7,8,9,10-hexahydro-2-hydroxy-N'-(2-phenylethyl)-6,9-methanobenzocyclooctene-11-carboxamide and (5'R,11'R), (5'S,11'S)-1',2',3',4',5',6'-hexahydro-8'-hydroxy-1-(2-phenylethyl)spiro(1H-imidazo-4,11'-(2,5)methanobenzocycloocten)-5(4H)-one The formamidoamide obtained in Step 4 above (1.5 g.) is dissolved in methanol (40 ml.) and concentrated hydrochloric acid (15 ml.) and stirred 20 hours at room temperature. The mixture is concentrated in vacuo to remove most of the methanol, neutralized with 10% sodium hydroxide, and then made basic with saturated sodium bicarbonate. The mixture is extracted with chloroform, and the extracts are dried ($Na_2SO_4$) and reduced to dryness to yield a residue (1.5 g.) which is chromatographed on silica gel (50 g.). Elution with chloroform, then chloroform containing a trace of methanol provided first pure (5′R, 11′R), (5′S,11′S)-1′,2′, 3′, 5′,6′-hexahydro-8′-hydroxy-1-(2-phenylethyl)-spiro(1H-imidazo-4,11′-(2,5)methanobenzocycloocten)-5(4H)-one (210 mg.), then pure d,l-11-endo-amino-5,6,7,8,9,10-hexahydro-2-hydroxy-N′-(2-phenylethyl)-6,9-methanobenzocyclooctene-11-carboxamide (1.205 g.).

d,l-11-endo-Amino-5,6,7,8,9,10-hexahydro-2-hydroxy-N′-(2-phenylethyl)-6,9-methanobenzocyclooctene-11-carboxamde crystallizes from chloroform-hexane, m.p. 118°–119° C.

IR(KBr): 3500, 3400, 3300-2500, 1640 $cm^{-1}$.

NMR ($CDCl_3$): δ1.2 (2H, broad m), 1.85 (2H, broad), 2.1-4.0 (14H, complex, peak at 3.7 disappears on addition of $D_2O$ accounting for 3H), 6.5-7.4 (9H, complex with 5H singlet at 7.20).

mass spectrum: m/e 350 (M+), 305, 202 (base peak), 185, 171.

Anal. Calcd. for $C_{22}H_{26}N_2O_2$: C, 75.40; H, 7.48; N, 7.98. Found: C, 75.67; H, 7.63; N, 8.19.

This compound (1.2 g.) is dissolved in methanol (5 ml.) made slightly acidic with methanolic HCl, and concentrated to ca. 1 ml., then diluted with chloroform. The crystals are separated and collected (1.3 g). The material is twice recrystallized from methanol-chloroform to yield analytically pure compound (1.02 g.), m.p. 276°–278° C.

Anal. Calcd. for $C_{22}H_{27}N_2O_2Cl$: C, 68.29; H, 7.03; N, 7.24; Cl, 9.16. Found: C. 68.71; N, 7.24; N, 7.41; Cl, 9.47.

(5′R,11′R), (5′S,11′S)-1′,2′,3′, 4′,5′,6′-hexahydro-8′-hydroxy-1-(2-phenylethyl)spiro(1H-imidaza-4,11′-(2,5)methanobenzocycloocten)-5(4H)-one recrystallizes from chloroform-hexane, m.p. 210°–211° C. to give an analytical sample.

IR(film): 3200, 1725 $cm^{-1}$.

$^1$H-NMR ($CDCl_3$): 1.3 (2H, m), 1.4-3.9 (12H, complex), 5.9 (1H, broad, exchanged by $D_2O$, phenol OH), 6.3-7.1 (3H, m), 7.2 (5H, s), 7.35 (1H, s).

mass spectrum: m/e 360 (M+), 305, 202.

Anal. Calcd. for $C_{23}H_{24}N_2O_2$: C, 76.64; H, 6.71; N, 7.77. Found: C, 76.62; H, 6.80; N, 7.98. This compound can be prepared directly: d,l-11-endo-amino-5,6,7,8,9,10-hexahydro-2-hydroxy-N′-(2-phenylethyl)-6,9-methanobenzocyclooctene-11-carboxamide (1.32 g., 3.5 mM) is stirred in phosphorous oxychloride (20 ml.) at room temperature overnight. The volatiles are removed in vacuo, the residue is diluted with methanol (50 ml.) and then made basic with $NaHCO_3$ (1N). The mixture is extracted with chloroform (75 ml.) and 25% methanol-chloroform (100 ml.), and the combined extracts are dried and evaporated to give an oil (2.5 g.). Chromatography on silica gel, eluting with 1% methanol-chloroform gives the product (75% yield), m.p. 203°–204° C. (from ether).

EXAMPLE 4

11-endo-Amino-5,6,7,8,9,10-hexahydro-6,9-methanobenzocyclooctene

The ketone 5,6,7,8,9,10-hexahydro-6,9-methanocycloocten-11-one (1 g.) is refluxed with hydroxylamine hydrochloride (1.1 g.) for 2 hours. The ethanol is evaporated and water is added (5 ml.). The resultant crystals are filtered off, washed with cold water, and recrystallized from methanol-water (yield 1.1 g.).

The oxime (900 mg.) is hydrogenated over Adams catalyst (90 mg.) in glacial acetic acid (50 ml.) at 20 psi for 2.5 hours. The mixture is filtered, reduced to dryness, taken up in water, and basified with saturated $NaHCO_3$. Extraction with chloroform yields, after evaporation of the solvents, the title amine as an oil (780 mg.).

IR(film): 330 $cm^{-1}$.

$^1$H-NMR($CDCl_3$): 0.9-1.8 (6H becoming 4H on $D_2O$ exchange, complex m), 2.0-2.8 (6H, m), 3.22 (3H, d over m, d:j=14 Hz), 6.95 (4H, s).

The compound is taken up in methanol and treated with methanolic HCl, reduced to dryness, and recrystallized from hot chloroform-methanol (soluble in the cold?) to give the compound hydrochloride (700 mg.), m.p. 285° C. (sublimes). mass spectrum: m/e 187 (M+, base peak), 186, 170, 158, 142, 129.

Anal. Calcd. for $C_{13}H_{16}NCl$: C, 69.82; H, 8.11; N, 6.26; Cl, 15.85. Found: C, 69.85; H, 8.12; N, 6.52; Cl, 16.07.

EXAMPLE 5

Preparation of d,l-11-endo-Amino-6,9-dimethyl-5,6,7,8,9,10-hexahydro-6,9-methanobenzocyclooctene Step 1: 6,9-Dimethyl-5,6,7,8,9,10-hexahydro-6,9-methanobenzocycloocten-11-one α,α′-Dibromoxylene (30.3 g., 0.115 Mole) is dissolved in dry acetonitrile (250 ml.) and then, under nitrogen, the pyrrolidine enamine of 2,5-dimethylcyclopentanone (prepared from 2,5-dimethylcyclopentanone and pyrrolidine via the method of Stork) is added dropwise over one-half hour. The mixture is refluxed 2 days, cooled, water (100 ml.) is added; and the mixture is refluxed 1 hour, cooled, concentrated in vacuo, then extracted with ether (3×75 ml.). The combined extracts are washed with 10% HCl (50 ml.), brine (50 ml.), then dried and evaporated to yield 16 g. of solid, which recrystallized from dichloroethane-hexane gives pure title compound (9.7 g.). The mother liquors are chromatographed on silica gel (100 g.), eluting with ether-hexane (1:4) to give 5.8 g. more title compound, which yields 4.9 g. pure on crystallization from ether-hexane (64% total yield), m.p. 134°–135° C.

IR (KBr): 1730 $cm^{-1}$.

$^1$H-NMR ($CDCl_3$): δ1.20 (6H, s), 1.45 (4H, s), 2.67 (4H, $A_2B_2q$, J=16 Hz), 7.20 (4H, s).

Step 2: d,l-6,9-Dimethyl-5,6,7,8,9,10-hexahydro-2-hydroxy-6,9-methanobenzocycloocten-11-one The ketone obtained in Step 1 above (5 g., 28 mM) is dissolved in trifluoroacetic acid (TFA) (100 ml.), and thallium tris-trifluoroacetate (19 g., 35 mM) is added; and the mixture is stirred under nitrogen overnight. Lead tetraacetate (15.5 g., 35 mM) is added (in 20 ml. TFA), and the mixture is stirred 1 hour at room temperature and 1 hour at reflux. The mixture is cooled, triphenylphosphine (9.5 g.) is added; and the mixture is stirred 15 minutes, then reduced to dryness. 6N HCl (100 ml.) and chloroform (100 ml) are added, and the mixture is stirred 10 minutes, then filtered through celite. The filter cake is washed with chloroform (100 ml.), and the combined filtrates are separated, and the aqueous layer is washed with chloroform (2×50 ml.). The combined organic layers are extracted with 2N NaOH (3×50 ml.). The basic extracts are washed with chloroform (2×15 ml.), then acidified with 6N HCl (50 ml.) and extracted with chloroform (50 ml.) and chloroform-10% methanol (2×50 ml.). These extracts are washed with brine, dried, and evaporated to provide crude title product (2.9 g.). Chromatography on silica (125 g.), eluting with dichloromethane, gives pure title compound (1.8 g.). Recrystallization from chloroform-hexane gives an analytical sample; m.p. 201.5°–202° C.

IR (KBr): 3370; 1725 cm$^{-1}$.

$^1$H-NMR(CDCl$_3$): δ1.20 (6H, s), 1.50 (4H, s), 2.6 (4H, m), 5.7 (1H, broad, exchanged by CD$_3$OD), 6.6-7.1 (3H, m).

Step 3: Oxime from d,l-6,9-dimethyl-5,6,7,8,9,10-hexahydro-2-hydroxy-6,9-methanobenzocycloocten-11-one The ketone obtained in Step 2 above (1 g.) is refluxed with hydroxylamine hydrochloride (1 g.), pyridine(2 ml.), and ethanol (10 ml.) for 1 hour. The mixture is cooled, poured into water (50 ml.), and extracted with chloroform (3×25 ml.). The extracts are dried (N$_2$SO$_4$) and reduced to dryness in vacuo (1.1 g. residue). The resultant solid is recrystallized from chloroform-hexane to give pure oxime (1.05 g.), m.p. 216°–217° C.

IR (KBr): 3380, 1650 cm$^{-1}$.

$^1$H-NMR(COCl$_3$-MeOH-d$_4$): δ1.23 (3H, s), 1.46 (4H, s), 1.63 (3H, s), 2.3-3.5 (4H, complex m), 4.3 (2H, exchanged by D$_2$O), 6.5-7.1 (3H, m).

Step 4: d,l-11-endo-Amino-6,9-dimethyl-5,6,7,8,9,10-hexahydro-6,9-methanobenzocyclooctene The oxime obtained in Step 3 above (950 mg.) is hydrogenated over Adams catalyst at 30 psi in glacial acetic acid for 3 hours. The mixture is filtered, reduced to dryness, taken up in 5% HCl solution, and then washed with dichloromethane (2×20 ml.). The aqueous solution is made basic with a saturated solution of sodium bicarbonate, then extracted with 10% methanol-chloroform (3×50 ml.); then the extracts are dried and reduced to dryness (950 mg.). A portion (100 mg.) recrystallized from chloroform-hexane gives pure title compound (30 mg.), m.p. 214°–216° C.

IR (KBr): 3380 cm$^{-1}$.

H$^1$-NMR(CDCl$_3$-MeOH-d$_4$): δ1.10 (6H, s), 1.33 (4H, s), 2.10 (2H, d, J=16 Hz), 2.56 (1H, s), 2.96, 3.00 (2H, two overlapping d, J=J=16 Hz), 4.5 (3H, s, exchanged by d$_2$O), 6.4-7.0 (3H, m).

The above mother liquors and thereserved amine are taken up in methanol and treated with gaseous HCl, reduced to dryness; and the resultant solid is recrystallized from methanol-ethylacetate to yield analytically pure title compound hydrochloride as a hemi-hydrate; m.p. 265° C.

IR (KBr): 3500-2500 cm$^{-1}$.

H$^1$-NMR (MeOH-d$_4$): δ1.1 (6H, s), 1.3 (4H, s), 2.3 (2H, d, J=16 Hz), 2.95, 3.0 (2H, 2d), 3.05 (1H, s), 6.3-6.9 (3H, m).

Anal. Calcd. for C$_{15}$H$_{21}$NO·HCl ½H$_2$O: C, 65.09; H, 8.37; N, 5.06; Cl, 12.81. Found: C, 65.39; H, 8.76; N, 4.92; Cl, 12.91.

EXAMPLE 6

Preparation of d,1-11-endo-amino-11-exo-(phenoxymethyl-, phenylmethyloxymethyl-, and phenylethyloxymethyl-)-2-hydroxy-5,6,7,8,9,10-hexahydro-6,9-methanobenzocyclooctene Step 1: d, 1-11-endo-amino-11-exo-hydroxymethyl-2-hydroxy-5,6,7,8,9,10-hexahydro-6,9-methanobenzocyclooctene To d,l-11-endo-11-exo-carboxy-2-hydroxy-5,6,7,8,9,10-hexahydro-6,9-methanobenzocyclooctene (5.0 g; 20.2 mmoles) in 100 ml. anhydrous tetrahydrofuran was added, dropwise at 0° C., a diborane solution (110 ml. 94 mmoles). The mixture was refluxed for approximately three hours. Water was carefully added until gas evolution stopped. This solution was evaporated to dryness and the residue was treated with methanol (110 ml.) and evaporated. This procedure was repeated three times. The mixture was then acidified with 1N hydrochloric acid and taken to dryness. The solid was triturated several times with 15% methanol in chloroform. The salts were filtered off and the filtrate was evaporated to dryness to yield d,l-11-endo-amino-11-exo-hydroxymethyl-2-hydroxy-5,6,7,8,9,10-hexahydro-6,9-methanobenzocyclooctene hydrochloride (5.3 g; 93%) melting point: 295° C.

Elemental analysis for C$_{14}$H$_{19}$NO$_2$HCl: Calculated: C: 62.33; H: 7.47; N: 5.19; Cl: 13.14: Found: C: 62.04; H:7.44; N: 5.26; Cl: 13.22.

Step 2: d,l-N-tosylaziridine-11-endo-spiro-2-tosyloxy-5,6,7,8,9,10-hexahydro-6,9-methanobenzocyclooctene D,l-11-endo-amino-11-exo-hydroxymethyl-2-hydroxy-5,6,7,8,9,10-hexahydro-6,9-methanobenzocyclooctene hydrochloride (13.3 g; 47 mmoles) and tosyl chloride (71 g; 375 mmoles) in 500 ml. pyridine were stirred at room temperature for 18 hours. The reaction mixture was evaporated to dryness and the residue was dissolved in 500 ml. chloroform. The organic layer was washed with 100 ml. water, with 100 ml. 1N hydrochloric acid and 100 ml. water. The chloroform solution was dried over sodium sulfate. Evaporation to dryness yielded a gum that was dissolved in dimethylformamide and stirred for 30 minutes at room temperature. The mixture was diluted with ether and then washed three times with water. The organic layer was dried over sodium sulfate and evaporated to yield d,l-N-tosylaziridine-11-endo-spiro-2-tosyloxy-5,6,7,8,9,10-hexahydro-6,9-methanobenzocyclooctene (16.0 g; 65%); melting point: 188°–189° C.

Elemental analysis for C$_{28}$H$_{29}$NO$_5$S: Calculated: C: 64.22; H: 5.58; N: 2.67; S: 12.24; Found: C: 64.09; H: 5.73; N: 2.56; S: 11.82.

Step 3: d,l-11-endo-tosylamino-11-exo-(phenoxymethyl-, phenylmethyloxymethyl-, and phenylethyloxymethyl-)-2-hydroxy-5,6,7,8,9,10-hexahydro-6,9-methanobenzocyclooctene The aziridine compound of Step 2 (3.6 mmoles) is added to a mixture of phenoxide, phenylmethoxide, or phenylethoxide, prepared by reacting a 50% sodium hydride dispersion (1.8 g: 37.5 mmoles) with phenol, phenylmethanol, or phenylethanol, respectively (39 mmoles), in 50 ml. dimethylformamide. The mixture is stirred at room temperature for 1 hour and then at 65° C. for an additional hour. The mixture is then poured onto 250 ml. water and acidified with 1N hydrochloric acid. The mixture is extracted with chloroform, and then washed several times with water. The organic layer is dried over sodium sulfate and concentrated under vacuum. The products crystallize from petroleum ether and are collected by filtration. The melting points for the three products prepared in this matter were as follows:

| | |
|---|---|
| phenoxymethyl- | 238°–240° C. |
| phenylmethyloxymethyl- | 200°–203° C. |
| phenylethyloxymethyl- | 188°–190° C. |

Step 4: d,l-11-endo-amino-11-exo-(phenoxymethyl-, phenylmethyloxymethyl-, and phenylethyloxymethyl-)-2-hydroxy-5,6,7,8,9,10-hexahydro-6,9-methanobenzocyclooctene The removal of the tosyl group from the product of Step 3 is carried out by treatment with sodium in liquid ammonia. To the tosylamide (3.4 mmoles) dissolved in tetrahydrofuran (45 ml.) is added ammonia (approx. 50 ml.) and then sodium metal (1.9 g; 82 mmoles). The mixture is stirred for 10 minutes. Ammonium chloride (12.4 g; 0.23 mole) is then added in small portions. The ammonia is permitted to evaporate off and the residue is taken up in 1N sodium bicarbonate and extracted with ethyl acetate. The organic layer is dried over sodium sulfate and evaporated to dryness. The residue is taken up in methanolic hydrogen chloride. Ether is added to the cloud point. The solution is left in a refrigerator, and the crystals are collected by filtration, washed with ether, and dried under vacuum. The melting points and elemental analysis for two of the products prepared in this manner were as follows:

| | | |
|---|---|---|
| phenoxymethyl | 186° (HCl) | C: 66.01 H: 7.20 N: 3.84 Cl: 9.74 C: 66.27 H: 7.39 N: 3.83 Cl: 10.21 |
| phenylethyloxymethyl | 213–216° C. (HCl) | C: 70.86 H: 7.54 N: 3.74 Cl: 9.48 C: 70.52 H: 7.61 N: 3.61 Cl: 9.43 |

What is claimed is:
1. A compound of the formula:

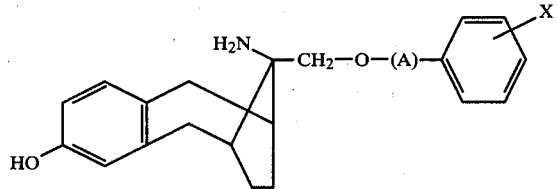

wherein
A is absent or is a lower alkylene substituent of from 1–3 carbons, and X is hydrogen; halo; $C_{1-4}$alkyl; $C_{1-4}$alkoxy; amino, and mono- and di-$C_{1-4}$alkyl substituted amino; cyano; trifluoromethyl; trifluoromethylthio; $C_{1-4}$alkylthio; $C_{1-4}$alkylsulfoxide; or $C_{1-4}$alkylsulfone.
2. The compound of claim 1 which is
(a) d,l-11-endo-amino-11-exo-phenoxymethyl-2-hydroxy-5,6,7,8,9,10-hexahydro-6,9-methanobenzocyclooctene;
(b) d,l-11-endo-amino-11-exo-phenylmethyloxymethyl-2-hydroxy-5,6,7,8,9,10-hexahydro-6,9-methanobenzocyclooctene; or
(c) d,l-11-endo-amino-11-exo-phenylethyloxymethyl-2-hydroxy-5,6,7,8,9,10-hexahydro-6,9-methanobenzocyclooctene.

* * * * *